United States Patent
Banke

(10) Patent No.: US 9,347,080 B2
(45) Date of Patent: May 24, 2016

(54) USE OF BROWNED GLUCOSE AS A FEED SUBSTRATE

(75) Inventor: Niels Banke, Soeborg (DK)

(73) Assignee: NOVOZYMES A/S, Bagsvaerd (DK)

( * ) Notice: Subject to any disclaimer, the term of this patent is extended or adjusted under 35 U.S.C. 154(b) by 6 days.

(21) Appl. No.: 13/982,678

(22) PCT Filed: Jan. 25, 2012

(86) PCT No.: PCT/EP2012/051084
§ 371 (c)(1),
(2), (4) Date: Jul. 30, 2013

(87) PCT Pub. No.: WO2012/104176
PCT Pub. Date: Aug. 9, 2012

(65) Prior Publication Data
US 2013/0309722 A1 Nov. 21, 2013

Related U.S. Application Data

(60) Provisional application No. 61/438,217, filed on Jan. 31, 2011.

(30) Foreign Application Priority Data

Jan. 31, 2011 (EP) .................................. 11152693

(51) Int. Cl.
*C12P 21/02* (2006.01)
*C12N 1/38* (2006.01)
*C12P 17/16* (2006.01)

(52) U.S. Cl.
CPC . *C12P 21/02* (2013.01); *C12N 1/38* (2013.01); *C12P 17/165* (2013.01)

(58) Field of Classification Search
CPC .......... C12P 21/02; C12P 17/165; C12N 1/38
See application file for complete search history.

(56) References Cited

U.S. PATENT DOCUMENTS 6,140,078 A * 10/2000 Sanders et al. ............... 435/69.1
2008/0026425 A1* 1/2008 Sun et al. .................... 435/69.1

OTHER PUBLICATIONS

Kumar et al., Methods for Pretreatment of Lignocellulosic Biomass for Efficient Hydrolysis and Biofuel Production, Ind. Eng. Chem. Res. (2009) 48, pp. 3713-3729.*
Schell et al., Dilute-Sulfuric Acid Pretreatment of Corn Stover in Pilot-Scale Reactor, Investigation of Yields, Kinetics, and Enzymatic Digestibilities of Solids; Applied Biochemistry and Biotechnology, (2003), vol. 105-108, pp. 69-85.*
Bowers et al, 1962, Antonie Van Leeuwenhoek 435-444.
Chen et al, 1992, Proc Biochem 27(6), 327-334.
Fetzer et al, 1953, Indust Engg Chem 45(5), 1075-1083.
Fulmer et al, 1931, J Bacteriol 21(4), 299-303.
Huang et al, 2010, Bio Res Technol 102(3), 3322-3329.
Johnson et al, 2007, Physiol Mol Plant Pathol 71(1-3), 18-25.
Pilath et al, 2010, J Agri Food Chem 58(10), 6131-6140.
Ramsey et al, 1956, J Bacteriol 72(4), 511-518.
Wach et al, 2007, Arch Microbiol 188(1), 81-88.

* cited by examiner

*Primary Examiner* — Karen Cochrane Carlson
*Assistant Examiner* — Jennifer M. H. Tichy
(74) *Attorney, Agent, or Firm* — Michael W. Krenicky

(57) ABSTRACT

A method for fermenting a microorganism, producing a compound of interest, in a culture medium comprising: adding a browned glucose solution to the culture medium, wherein the browned glucose solution is a glucose solution that has been acid treated and heated to a temperature of at least 90 degrees Celsius, and wherein the glucose solution has a concentration of at least 500 g/l.

16 Claims, No Drawings

USE OF BROWNED GLUCOSE AS A FEED SUBSTRATE

CROSS-REFERENCE TO RELATED APPLICATIONS

This application is a 35 U.S.C. 371 national application of PCT/EP2012/051084 filed Jan. 25, 2012, which claims priority or the benefit under 35 U.S.C. 119 of European application no. 11152693.5 filed Jan. 31, 2011 and U.S. provisional application No. 61/438,217 filed Jan. 31, 2011, the contents of which are fully incorporated herein by reference.

TECHNICAL FIELD

The present invention relates to a method of increasing the yield of a compound of interest in a fermentation using browned glucose as a feed substrate.

BACKGROUND ART

Commercially it is of key importance continuously to increase the yield of a compound of interest produced by microbial fermentation in industrial scale.

If productivity can be increased this will liberate production capacity for other compounds and reduce the need for new investments in production.

It is known (Process Biochemistry, vol. 27, no. 6, 1992, page 327-334) that acid hydrolysed starch may be an inducer for cellulase production by *Trichoderma reesei*.

SUMMARY OF THE INVENTION

It has surprisingly been found that the yield of a compound of interest may be increased very significantly by adding a browned glucose solution to the culture medium, so we claim:
A method for fermenting a microorganism, producing a compound of interest, in a culture medium comprising:
adding a browned glucose solution to the culture medium, wherein the browned glucose solution is a glucose solution that has been acid treated and heated to a temperature of at least 90 degrees Celsius, and wherein the glucose solution has a concentration of at least 500 g/l.

DETAILED DISCLOSURE OF THE INVENTION

The present invention deals with increasing the yield of a product of interest in industrial fermentations.

The microorganism may be any microorganism useful for industrial fermentations, in particular a bacterium or a fungus.

Bacterium

The bacterium expressing the compound of interest according to the invention may be a bacterium of any genus.

In a preferred embodiment, the compound of interest may be obtained from a gram positive bacterium, in particular from a *Bacillus* or a *Streptomyces* strain.

In a preferred embodiment the *Bacillus* strain is selected from the group consisting of *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, and *Bacillus thuringiensis*.

In another preferred embodiment the *Streptomyces* strain is selected from the group consisting of *Streptomyces scabies, Streptomyces lividans, Streptomyces turgidiscabies, Streptomyces murinus*, and *Streptomyces acidiscabies*; in particular the *Streptomyces* strain is selected from the group consisting of *Streptomyces scabies, Streptomyces acidiscabies*, and *Streptomyces turgidiscabies*; especially the *Streptomyces* strain is a *Streptomyces acidiscabies* strain.

The compound of interest may be obtained from a gram negative bacterium, in particular from an *Escherichia* sp. strain, e.g., *Escherichia coli*, or from a *Pseudomonas* sp. strain.

Fungus

The fungus expressing the compound of interest according to the invention may be a fungus of any genus including yeast. In a preferred embodiment the fungus is a filamentous fungus.

According to the invention the fungus may especially be a filamentous fungal strain selected from the group consisting of *Achlya, Acremonium, Aspergillus, Aureobasidium, Cephalosporium, Cochliobolus, Cryptococcus, Endothia, Filibasidium, Fusarium, Humicola, Magnaporthe, Mucor, Myceliophthora, Neocallimastix, Neurospora, Paecilomyces, Penicillium, Piromyces, Podospora, Pyricularia, Schizophyllum, Talaromyces, Thermoascus, Thielavia, Tolypocladium*, and *Trichoderma*, in particular the fungus may be from the group consisting of *Achlya, Aspergillus, Cephalosporium, Cochliobolus, Endothia, Fusarium, Humicola, Mucor, Neurospora, Penicillium, Podospora, Pyricularia*, and *Trichoderma*.

In another preferred embodiment the fungus is an *Aspergillus* strain, in particular the fungus is selected from the group consisting of *Aspergillus aculeatus, Aspergillus awamori, Aspergillus foetidus, Aspergillus japonicus, Aspergillus nidulans, Aspergillus niger*, and *Aspergillus oryzae*.

In an especially preferred embodiment the fungus is a *Trichoderma* strain, particularly a *Trichoderma reseeii* strain.

Bacterial and fungal strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

Compound of Interest

The compound of interest according to the invention may be any valuable compound produced by a microorganism, in particular a secondary metabolite.

The compound may be a phytotoxin such as a thaxtomin. The compound of interest may also be a therapeutic protein, or an enzyme (e.g., a hydrolase, a transferase, a lyase, an isomerase, or a ligase; in particular a cellulase).

The compound of interest according to the invention may be an antibiotic such as penicillin or cephalosporin or erythromycin, or a commodity chemical such as citric acid.

Thaxtomin

A compound of interest according to the invention may be a thaxtomin. Thaxtomins are a known group of phytotoxins.

Thaxtomins include any of the type from a family of cyclic dipeptides, such as 4-nitroindol-3-yl-containing 2,5-dioxopiperazines. Suitable thaxtomins include agents described as cyclic dipeptides having the basic structure cyclo-(L-4-nitrotryptophyl-L-phenylalanyl). In embodiments, suitable diketopiperazine moieties may be N-methylated, and include congeners carrying phenylalanyl alpha- and ring-carbon hydroxyl groups. Non-limiting examples of suitable thaxtomins for use in accordance with the present invention include thaxtomin A, thaxtomin A ortho isomer, thaxtomin B, and C-14 deoxythaxtomin B (thaxtomin D), and derivatives of any of these.

Thaxtomins include the following formula:

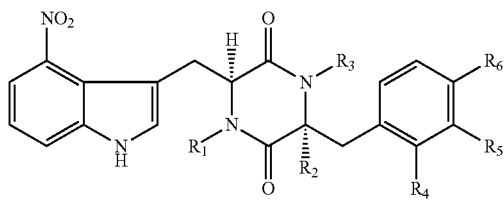

In embodiments, $R_1$ is methyl or H.
In embodiments, $R_2$ is hydroxy or H.
In embodiments, $R_3$ is methyl or H.
In embodiments, $R_4$ is hydroxy or H.
In embodiments, $R_5$ is hydroxy or H.
In embodiments, $R_6$ is hydroxy or H.
In embodiments, $R_1$ is methyl, $R_2$ is hydroxy, $R_3$ is methyl, $R_4$ is H, $R_5$ is hydroxy and $R_6$ is H.
In embodiments, $R_1$ is methyl, $R_2$ is hydroxy, $R_3$ is methyl, $R_4$ is hydroxy, $R_5$ is H and $R_6$ is H.
In embodiments, $R_1$ is methyl, $R_2$ is H, $R_3$ is H, $R_4$ is H, $R_5$ is H and $R_6$ is H.
In embodiments, $R_1$ is methyl, $R_2$ is hydroxy, $R_3$ is methyl, $R_4$ is H, $R_5$ is H and $R_6$ is H.
In embodiments, $R_1$ is methyl, $R_2$ is H, $R_3$ is methyl, $R_4$ is H, $R_5$ is H and $R_6$ is H.
In embodiments, $R_1$ is methyl, $R_2$ is hydroxy, $R_3$ is H, $R_4$ is H, $R_5$ is H and $R_6$ is H.
In embodiments, $R_1$ is methyl, $R_2$ is hydroxy, $R_3$ is methyl, $R_4$ is H, $R_5$ is H and $R_6$ is hydroxy.
In embodiments, $R_1$ is methyl, $R_2$ is hydroxy, $R_3$ is methyl, $R_4$ is H, $R_5$ is hydroxy and $R_6$ is hydroxy.
In embodiments, $R_1$ is methyl, $R_2$ is hydroxy, $R_3$ is H, $R_4$ is H, $R_5$ is hydroxy and $R_6$ is H.
In embodiments, $R_1$ is H, $R_2$ is hydroxy, $R_3$ is methyl, $R_4$ is H, $R_5$ is hydroxy and $R_6$ is H.
In embodiments, $R_1$ is H, $R_2$ is H, $R_3$ is H, $R_4$ is H, $R_5$ is H and $R_6$ is H.

Thaxtomin A is composed of 4-nitroindol-3-yl-containing 2,5-dioxopiperazine and is the predominant thaxtomin produced by *Streptomyces scabies*, *Streptomyces acidiscabies*, and *Streptomyces turgidiscabies*, with phenylalanyl m-ring and alpha-C hydroxyl additions. The chemical composition comprises, or consists of:

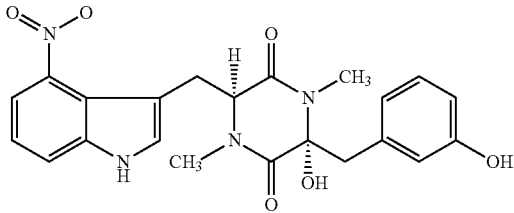

Proteins

A compound of interest according to the invention may be a protein.

In a preferred embodiment, the protein of interest is an enzyme, in particular a hydrolase (class EC 3 according to Enzyme Nomenclature; Recommendations of the Nomenclature Committee of the International Union of Biochemistry).

In a particular preferred embodiment the following hydrolases are preferred:

Amyloglucosidases: Amyloglucosidases (also called glucoamylases and glucan 1,4-alpha-glucosidase, EC 3.2.1.3) are enzymes which catalyze the release of D-glucose from the non-reducing ends of starch or related oligo- and polysaccharide molecules.

Suitable amyloglucosidases include those of fungal origin, especially those from filamentous fungi or yeasts, e.g., *Talaromyces emersonii*, *Aspergillus niger* and *Aspergillus awamori*.

Chemically modified or protein engineered mutants are included.

An example of a useful *Talaromyces emersonii* amyloglucosidase is described in WO 99/28448.

An example of a commercially available amyloglucosidase is AMG™ (Novozymes A/S).

Amylases: Suitable amylases (alpha and/or beta) include those of bacterial or fungal origin.

Chemically modified or protein engineered mutants are included. Amylases include, for example, alpha-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, WO 97/43424, and WO 01/66712, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Especially suitable amylases are the acid amylases of fungal origin, e.g., acid amylase from *Aspergillus niger*.

Commercially available amylases are DURAMYL™, TERMAMYL™, FUNGAMYL™, NATALASE™, TERMAMYL LC™, TERMAMYL SC™, LIQUIZYME-X™ and BAN™ (Novozymes A/S), RAPIDASE™ and PURASTAR™ (from Genencor International Inc.).

Cellulases: Suitable cellulases include those of bacterial or fungal origin. Chemically modified or protein engineered mutants are included. Suitable cellulases include cellulases from the genera *Bacillus*, *Pseudomonas*, *Humicola*, *Fusarium*, *Thielavia*, *Acremonium*, and *Trichoderma*, e.g., the fungal cellulases produced from *Humicola insolens*, *Myceliophthora thermophila*, *Fusarium oxysporum* and *Trichoderma reesei*; in particular cellulases from *Trichoderma reesei* are preferred; (examples are disclosed in U.S. Pat. No. 4,435,307, U.S. Pat. No. 5,648,263, U.S. Pat. No. 5,691,178, U.S. Pat. No. 5,776,757 and WO 89/09259).

Commercially available cellulases include CELLUCLAST™, CELLUZYME™, CAREZYME™, and CAREZYME CORE™ (Novozymes A/S), CLAZINASE™, and PURADAX HA™ (Genencor International Inc.), and KAC-500(B)™ (Kao Corporation).

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™, LIPOLASE ULTRA™ and LIPEX™ (Novozymes A/S).

Proteases: Suitable proteases include those of animal, vegetable or microbial origin. Microbial origin is preferred. Chemically modified or protein engineered mutants are included. The protease may be an acid protease, a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Preferred commercially available protease enzymes include ALCALASE™, SAVINASE™, PRIMASE™, DURALASE™, ESPERASE™, RELASE™ and KANNASE™ (Novozymes A/S), MAXATASE™, MAXACAL™, MAXAPEM™, PROPERASE™, PURAFECT™, PURAFECT OXP™, FN2™, and FN3™ (Genencor International Inc.).

Other preferred hydrolases: Other preferred hydrolases are carbohydrolases including MANNAWAY™ (Novozymes A/S).

Other hydrolases such as transferases, lyases, isomerases, and ligases may also be produced according to the invention.

Modification of the Microorganism of Interest

The microorganism producing the compound of interest has typically been transformed with an expression construct comprising a promoter operably linked to a gene encoding the compound of interest. Various promoters are used and described in the prior art.

It is normally also beneficial to have more than one copy of the compound encoding the compound of interest in order to make the yield as high as possible.

The promoter is preferably an inducible promoter.

Fermentations

The present invention may be useful for any fermentation in industrial scale, e.g., for any fermentation having culture media of at least 50 liters, preferably at least 100 liters, more preferably at least 500 liters, even more preferably at least 1000 liters, in particular at least 5000 liters.

The microorganism may be fermented by any method known in the art. The fermentation medium may be a complex medium comprising complex nitrogen and/or carbon sources, such as soybean meal, soy protein, soy protein hydrolysate, cotton seed meal, corn steep liquor, yeast extract, casein, casein hydrolysate, potato protein, potato protein hydrolysate, molasses, and the like. The fermentation medium may be a chemically defined media, e.g., as defined in WO 98/37179.

The fermentation may be performed as a batch, a fed-batch, a repeated fed-batch or a continuous fermentation process.

Carbon Limited Conditions

It may be an advantage according to the invention to use a carbon limited fermentation.

Carbon limited conditions mean that the microorganism has just enough carbon to grow with a specific growth rate wherein said specific growth rate is lower than the maximum specific growth rate.

Browned Glucose

The present invention discloses the surprisingly high advantage by adding a browned glucose solution to a culture medium instead of just adding a glucose solution to a culture medium.

The browned glucose solution is a glucose solution that has been acid treated and heated to a temperature of at least 90 degrees Celsius, and wherein the glucose solution has a concentration of at least 500 g/l.

In a preferred embodiment the glucose solution is first acid treated and then heated to a temperature of at least 90 degrees Celsius.

The glucose solution should have a high concentration of glucose. In a preferred embodiment the glucose solution has a concentration of least 500 g/l; preferably a concentration of at least 550 g/l; preferably a concentration of at least 600 g/l; preferably a concentration of at least 650 g/l; preferably a concentration of at least 700 g/l; preferably a concentration of at least 750 g/l; preferably a concentration of at least 800 g/l; preferably a concentration of at least 850 g/l; preferably a concentration of at least 900 g/l; preferably at least 950 g/l; preferably a concentration of at least 1000 g/l; preferably a concentration of at least 1050 g/l; preferably a concentration of at least 1100 g/l; in particular the glucose solution has a concentration of from 500 g/l to 1200 g/l; especially the glucose solution has a concentration of from 600 g/l to 1200 g/l; especially the glucose solution has a concentration of from 700 g/l to 1200 g/l; and even more preferably the glucose solution has a concentration of from 800 g/l to 1200 g/l.

Any acid known in the art may be used for the acid treatment. A preferred acid is phosphoric acid, sulphuric acid, hydrochloric acid, nitric acid, or citric acid; in particular phosphoric acid or sulphuric acid.

The acid treatment results in a glucose solution—before the heat treatment—with a pH less than 4.5; in particular with a pH less than 4.0; in particular with a pH less than 3.5; in particular with a pH less than 3.0; in particular with a pH less than 2.5; in particular with a pH less than 2.0; in particular with a pH less than 1.5; in particular with a pH less than 1.0; especially the pH is in the range of from pH 0.5 to pH 4.5; and even more preferably the pH is in the range of from pH 0.5 to pH 3.5.

The acid treated glucose solution is heated to a temperature of at least 90 degrees Celsius; in particular to a temperature of at least 95 degrees Celsius; in particular to a temperature of at least 100 degrees Celsius; in particular to a temperature of at least 101 degrees Celsius; in particular to a temperature of at least 102 degrees Celsius; in particular to a temperature of at least 103 degrees Celsius; in particular to a temperature of at least 104 degrees Celsius; in particular to a temperature of at least 105 degrees Celsius; in particular to a temperature of at least 106 degrees Celsius; in particular to a temperature of at least 107 degrees Celsius; in particular to a temperature of at least 108 degrees Celsius; in particular to a temperature of at least 109 degrees Celsius; in particular to a temperature of at least 110 degrees Celsius; in particular to a temperature of at least 111 degrees Celsius; in particular to a temperature of at least 112 degrees Celsius; in particular to a temperature of at least 113 degrees Celsius; in particular to a temperature of at least 114 degrees Celsius; in particular to a temperature of at least 115 degrees Celsius; in particular to a temperature of at least 116 degrees Celsius; in particular to a temperature of at least 117 degrees Celsius; in particular to a temperature of at least 118 degrees Celsius; in particular to a temperature of at least 119 degrees Celsius; in particular to a temperature of at least 120 degrees Celsius; in particular to a temperature of at least 121 degrees Celsius; in particular to a temperature of at least 122 degrees Celsius; in particular to a temperature of at least 123 degrees Celsius; in particular to a temperature of at least 124 degrees Celsius; in particular to a temperature of at least 125 degrees Celsius; in particular to a temperature of at least 130 degrees Celsius; in particular to a temperature of at least 135 degrees Celsius; preferably to a temperature in the range of from 90 to 135 degrees Celsius; in particular to a temperature in the range of from 100 to 135 degrees Celsius; and even more preferably to a temperature in the range of from 110 to 130 degrees Celsius.

The high temperatures are typically obtained by use of an autoclave. Various types of autoclaves are known in the art.

Recovery of the Compound of Interest

The product according to the invention may be a crude product; e.g., the product may be directly obtained from the fermentation broth.

A further aspect of the invention concerns the downstream processing of the fermentation broth. After the fermentation process is ended, the compound of interest may be recovered from the fermentation broth, using standard technology developed for the compound of interest.

The relevant downstream processing technology to be applied depends on the nature of the compound of interest.

A process for the recovery of a compound of interest from a fermentation broth will typically (but is not limited to) involve one or more of the following steps:
1) pre-treatment of broth (e.g., pH treatment and/or flocculation)
2) removal of cells and other solid material from broth (primary separation)
3) filtration
4) concentration
5) filtration
6) stabilization and standardization.

Apart from the unit operations listed above, a number of other recovery procedures and steps may be applied, e.g., variation in temperature, crystallization, treatment of the solution comprising the compound of interest with active carbon, and use of various adsorbents.

The invention is further illustrated in the following example, which is not intended to be in any way limiting to the scope of the invention as claimed.

Example 1

Effect of Browned Glucose on the Production of Thaxtomin A from *Streptomyces acidiscabies*

The following example shows that the use of a browned glucose solution, instead of a glucose solution, results in a strong induction of the thaxtomin A production in *Streptomyces acidiscabies*.

Media:
2 g/L Difco yeast extract
0.025 g/L CuSO4 5H2O
2.44 g/L Na2HPO4 monohydrate
7.5 g/L K2HPO4
2.5 g/L (NH4)2SO4
2 g/L Citric Acid
2.5 g/L MgSO4 7H2O
0.25 g/L CaCO3
3 g/L K2SO4
100 mM MES buffer (20 g/l)
Premix (trace elements solution—see recipe below) 10 mL/L
pH~6.0

500 ml glass Shake flasks with 2 baffels were used with 100 ml media.

0.1 ml P2000 antifoam was added to each flask.

Premix Trace Elements solution Recipe 0.4 g/L ZnSO4 7H2O
0.2 g/L CuSO4 5H2O
1.5 g/L FeSO4 7H2O
0.6 g/L MnSO4H2O
20 g/L Citric Acid After a heat treatment (121 degrees Celsius; 20 min) the carbohydrate source was added to the shake flasks.

Carbohydrate Sources:

2.44 ml glucose solution
820 g/l glucose, 1H2O; heat treated (autoclaved) 1 hr. at 121 degrees Celsius Or 2.13 ml browned glucose solution—acid and heat treated in the following way:
940 g/l glucose, 1H2O
87.2 g/l 16% H3PO4
0.6 g/l SB 2121 (antifoam)
Heat treated (autoclaved) for 1.5 hr. at 121 degrees Celsius The shake flasks were inoculated with 1 ml of a strongly growing inoculum culture (see details below).

Making Inoculum for the Cultivations:

The strain was inoculated from a cryo vial, and first grown on a PDA agar for 3 days at 28 degrees Celsius. A single colony was cut out of the agar and used for inoculation of a shake flask with the above described media and glucose as carbohydrate source. The shake flask was incubated for 2 days at 28 degrees Celsius 200 RPM; after 1 day the wall growth was shaken down into the media/culture by a short period of vigorous manual shaking. This culture was used for inoculums of the above described shake flasks.

The growth and production of thaxtomin A was measured after 2 days of cultivation:

| Carbohydrate source | Biomass [OD 650 nm] | Thaxtomin A [%] |
|---|---|---|
| Glucose | 10.7 | 100 |
| Browned glucose | 9.9 | 170 |

Conclusion:

Based on OD 650 which correlates well with the cell dry mass, the two carbon sources result in approximately the same level of biomass, while the level of thaxtomin A is surprisingly higher in the culture having browned glucose as the carbohydrate source.

The yield is 170% compared to the culture having glucose as carbohydrate source.

The invention claimed is:

1. A method for fermenting a microorganism, producing a compound of interest, in a culture medium comprising the steps of:

a) inoculating a culture medium in a fermenter with a microorganism capable of producing a compound of interest;
b) adding a browned glucose solution to the culture medium, wherein the browned glucose solution is a glucose solution that has been acid treated and heated to a temperature of at least 90 degrees Celsius, and wherein the glucose solution has a concentration of at least 500 g/l;
c) fermenting the microorganism to provide a fermentation broth; and
d) recovering the compound of interest from the fermentation broth.

2. The method according to claim 1, wherein the microorganism is a bacterium or a fungus.

3. The method according to claim 2, wherein the bacterium is selected from the group consisting of *Bacillus, Streptomyces, Escherichia*, and *Pseudomonas*.

4. The method according to claim 2, wherein the fungus is selected from the group consisting of *Achlya, Aspergillus, Cephalosporium, Cochliobolus, Endothia, Fusarium, Humicola, Mucor, Neurospora, Penicillium, Podospora, Pyricularia*, and *Trichoderma*.

5. The method according to claim 1, wherein the compound of interest is a secondary metabolite.

6. The method according to claim 1, wherein the compound of interest is a protein.

7. The method according to claim 6, wherein the protein is an enzyme.

8. The method according to claim 1, wherein the fermentation is a batch, a fed batch, a repeated fed batch or a continuous fermentation.

9. The method according to claim 1, wherein the acid treatment results in a glucose solution with a pH less than pH 4.5.

10. The method according to claim 1, wherein the glucose solution is acid treated and thereafter heated to a temperature of at least 90 degrees Celsius.

11. The method according to claim 1, wherein the glucose solution has a concentration of from 500 g/l to 1200 g/l.

12. The method according to claim 1, wherein the compound of interest is recovered after removal of the microorganism.

13. The method according to claim 5, wherein the secondary metabolite is Thaxtomin.

14. A method for fermenting a microorganism and producing a compound of interest in a culture medium comprising the steps of:
   a) inoculating a culture medium in a fermenter with a microorganism capable of producing a compound of interest;
   b) adding a browned glucose solution to the culture medium, wherein the browned glucose solution is a glucose solution that has been acid treated and heated to a temperature of at least 90 degrees Celsius, and wherein the glucose solution has a concentration of at least 500 g/l; and
   c) fermenting the microorganism to provide a fermentation broth.

15. The method according to claim 14, wherein the acid treated glucose solution has a pH less than pH 4.5.

16. The method according to claim 14, wherein the glucose solution has a concentration of from 500 g/l to 1200 g/l.

* * * * *